United States Patent [19]

Puderbaugh et al.

[11] 4,013,076

[45] Mar. 22, 1977

[54] ASPIRATOR JAR

[75] Inventors: George Puderbaugh, Manlius; Thomas S. Myers, Sherrill; Robert W. Pike, Syracuse; Robert B. Atley, Sherrill, all of N.Y.

[73] Assignee: Diemolding Corporation, Canastota, N.Y.

[22] Filed: Oct. 24, 1975

[21] Appl. No.: 625,770

Related U.S. Application Data

[63] Continuation-in-part of Ser. No. 587,613, June 17, 1975, abandoned.

[52] U.S. Cl. ............................................. 128/276
[51] Int. Cl.[2] ........................................ A61M 1/00
[58] Field of Search .......................... 128/275–278, 128/348, 297, DIG. 24, 276–278; 141/8, 59–61; 215/1 C; 220/634 R, 4 A, 4 B, 4 C, 4 E; 137/205; 417/118, 148; 15/353, 327 R

[56] References Cited

UNITED STATES PATENTS

| 961,816 | 6/1910 | Squier | 15/321 |
|---|---|---|---|
| 1,955,140 | 4/1934 | McKesson | 128/278 |
| 3,685,517 | 8/1972 | Reynolds et al. | 128/277 |
| 3,721,238 | 3/1973 | Wise et al. | 128/188 |
| 3,773,211 | 11/1973 | Bridgman | 128/276 |
| 3,805,788 | 4/1974 | Kleiner | 128/276 |
| 3,843,016 | 10/1974 | Bornhorst et al. | 128/276 |
| 3,859,998 | 1/1975 | Thomas et al. | 128/214.4 |
| 3,863,634 | 2/1975 | Reynolds et al. | 128/276 |

Primary Examiner—Robert W. Michell
Assistant Examiner—Henry S. Layton
Attorney, Agent, or Firm—Bruns & Jenney

[57] ABSTRACT

Medical suction apparatus for the collection of aspirated body fluid comprising a transparent, cylindrical container or jar having a mouth and a lid or closure which fits snugly over the mouth and which can be interlocked therewith by means of a locking bead on the peripheral edge of the container. A pair of upwardly extending nipples are molded integrally with the lid forming tubes therethrough, one nipple serving as a fluid inlet and the other acting as a vacuum conduit. A splash deflector chute is attached to the internal end of the fluid inlet tube to direct fluid toward the side of the container. A float-valve is connected to the inner end of the vacuum conduit to prevent passage of fluid into the vacuum line after the container is full.

The lid carries relief valve means for venting to the atmosphere when internal pressure drops to a predetermined level and the lid can be fitted with a vacuum line filter to prevent passage of entrained effluent into the vacuum system. The lid is provided with means for mounting a flexible plastic bag which extends downward into the container and is positioned to receive and retain the fluid effluent from the inlet port, thus providing a disposable flexible container and allowing for reuse of the rigid container.

1 Claim, 12 Drawing Figures

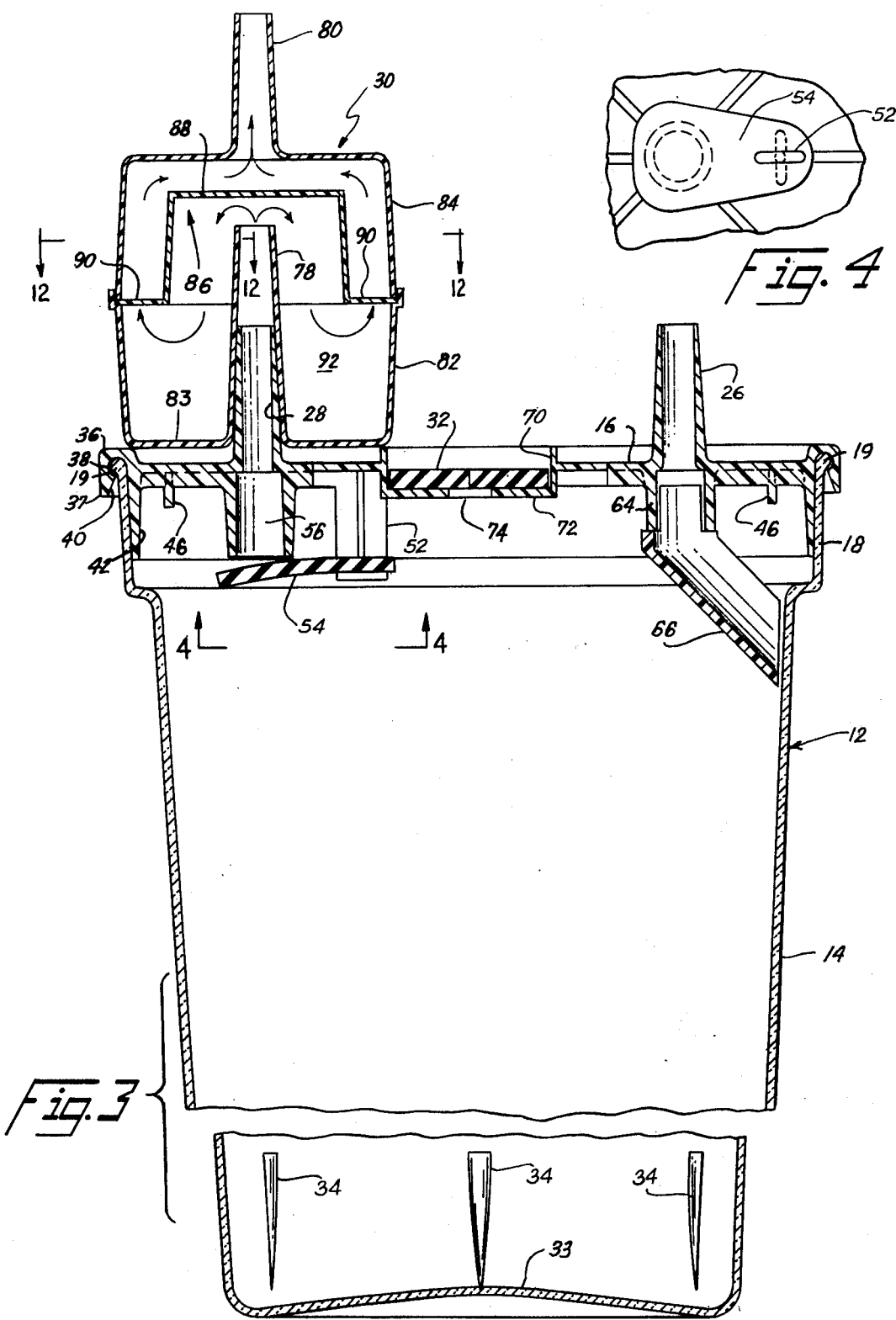

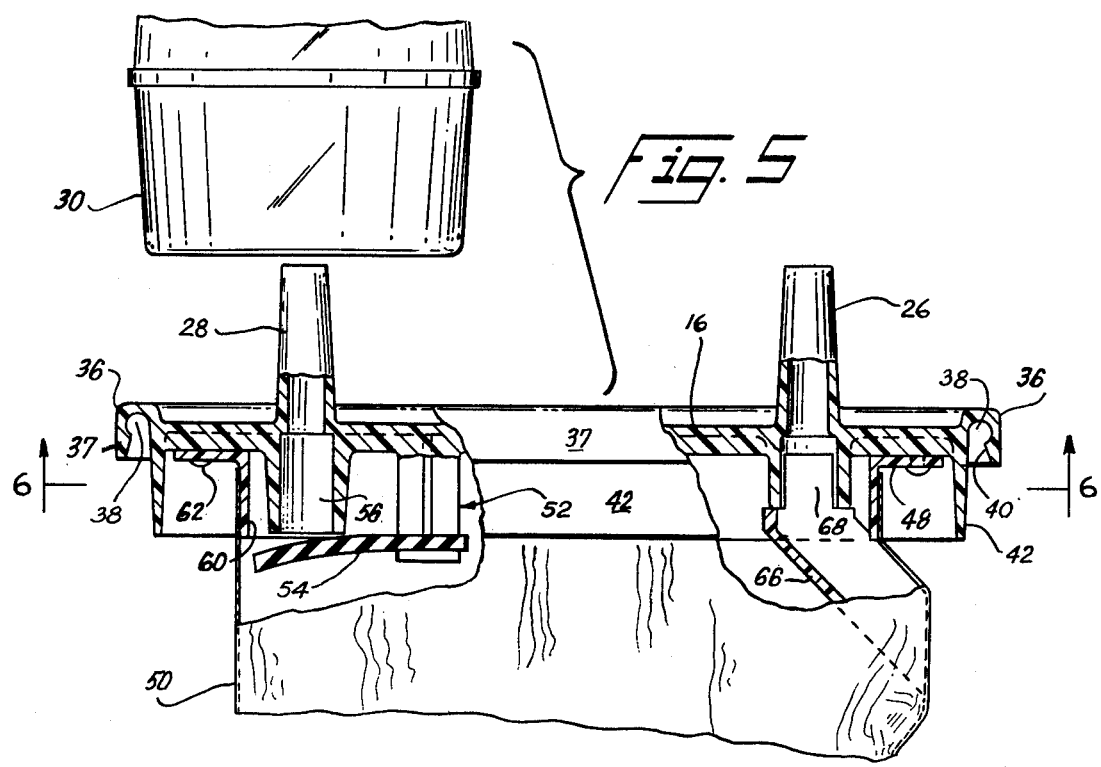
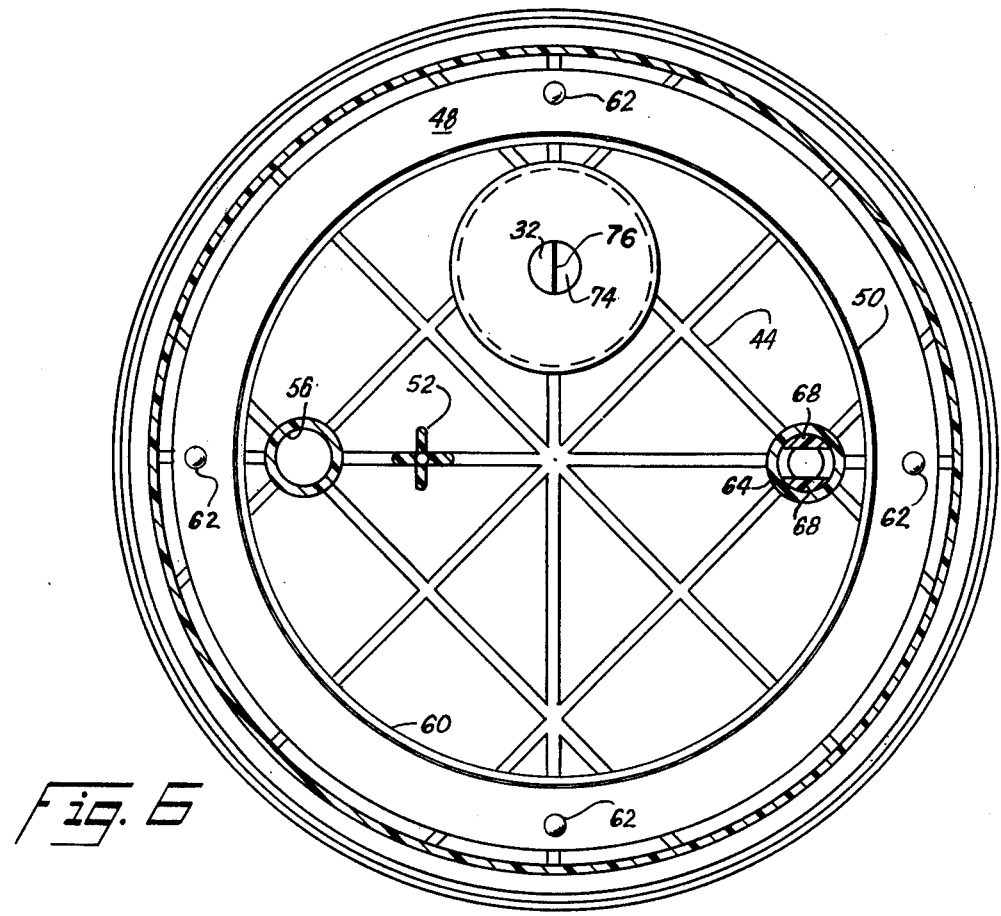

ASPIRATOR JAR

CROSS-REFERENCE TO RELATED APPLICATION

This application is a continuation-in-part of application Ser. No. 587,613, now abandoned filed June 17, 1975 by the same inventors.

BACKGROUND OF THE INVENTION

The present invention relates, in general, to medical and surgical apparatus for the collection of fluids, and more particularly to containers for receiving fluids from surgical patients.

As is well-known, during th course of a surgical operation on a patient, it is often necessary to remove from the site of the operation various body fluids, including blood, which tend to collect there. Removal of such body fluids is generally accomplished by means of an aspirator device which utilizes a vacuum to draw the fluids through a suitable tube for deposit in a collection bottle or jar. Body fluid storage bottles for use in such systems are well-known in the art, but have not been entirely satisfactory, since they have often been complex to assemble and use, expensive, and often unreliable in operation.

In an aspirator system, the vacuum which draws the fluid is produced in the fluid collection jar by some suitable means such as a central vacuum pump, thus causing a negative pressure in the tube leading to the patient from whom fluids are to be withdrawn. This vacuum draws the fluid through the drainage tube to the inlet port of the collection bottle. Since it is important in many cases to be able to monitor the flow of such fluids, it is important to measure the amount of fluid collected in the aspirator jar. For this purpose, the prior art has provided means for carrying this fluid to the bottom of the collection container, so that the inlet fluid does not splash and create a foam which would interfere with the volume measurements. However, such splash tubes have been found to create an additional problem, in that they can act as a siphon if for any reason the vacuum is lost and carry the aspirated fluids back to the operation site. Despite efforts to reduce the siphon effect, malfunction and flowback into the patient remains a serious problem.

Other problems found in prior art devices include a danger of contamination of the vacuum system by entrainment of moisture or small particles of solid matter. In addition, prior art devices have traditionally been constructed with walls of sufficient thickness to withstand substantial negative pressures without danger of implosion. Thin-walled collection vessels which are very desirable for economic reasons have generally been prone to malfunction as a result of implosion or cracking with resultant spillage of fluid and contamination of the operating area. Thus the availability of a thin-wall container with adequate protection against implosion, vacuum system contamination, and siphon flowback has become a major operating room need.

SUMMARY OF THE INVENTION

Briefly, the present invention comprises an aspirated body fulid collection apparatus comprising a closure or lid and a transparent, cylindrical container body portion formed with an upper edge having a locking bead thereon. The peripheral edge of the lid is provided with a pendant locking ring adapted to engage and receive the bead on the container and a pendant sealing flange adapted to engage the inner surface of the container wall to form a seal. This closure arrangement provides an airtight seal for the container and prevents accidental opening which could break the vacuum and interrupt the operation of the aspirator. Integrally molded as a part of the closure are a pair of spaced tubular ports or nipples, one serving as an inlet for aspirated body fluids and adapted to be connected to a fluid drainage tube leading from a patient and the other nipple acting as a vacuum conduit adapted to be connected to an external source of vacuum. Secured to the lid at the inner end of the inlet port so as to receive the aspirated fluid is a deflector chute, which directs the fluid flowing into the container against the sidewall of the container to effectively prevent splashing and foaming. The lid is also adapted to carry a plastic bag which acts as a liner for the container and receives the fluid which flows in via the inlet nipple and deflector chute. A float valve mechanism is secured to the lid at the inner end of the vacuum nipple so that the body fluids drawn into the container cannot flow out through the vacuum nipple into the vacuum line and source when the container is full.

In order to prevent contamination of the vacuum system and lines leading to the central vacuum pump by entrained fluid or solid matter the vacuum port is fitted with a removable filter which is designed to entrap contaminents without reducing the volume of air passing through the filter. The lid is also provided with a pressure relief valve which opens to prevent implosion of the container and also reduces the tendency of the fluids to foam or boil.

In addition the lid can be adapted to carry a conductive metal clip for connecting the tubing of the system in order to provide a completed electrical path thus minimizing electrical discharges.

The aspirator jar of the present invention is preferably molded from suitable plastic materials whereby a strong, lightweight, reliable, yet economic container is provided. This container meets the requirements of present aspirator systems and overcomes the difficulties of prior containers of this type.

BRIEF DESCRIPTION OF THE DRAWINGS

FIG. 3 is a fragmentary cross-sectional view of the container of FIG. 1 with filter, lid, and deflector chute in place;

FIG. 4 is a fragmentary bottom plan view of the lid showing the overflow valve viewed from line 4—4 of FIG. 3;

FIG. 5 is a fragmentary sectional view of the container lid with the flexible bag liner mounted in place and shown partially in elevation;

FIG. 6 is a bottom plan view of the container lid shown partially in section along line 6—6 of FIG. 5 showing the mounting arrangement of the flexible bag;

DESCRIPTION OF THE PREFERRED EMBODIMENT

Figure 1:
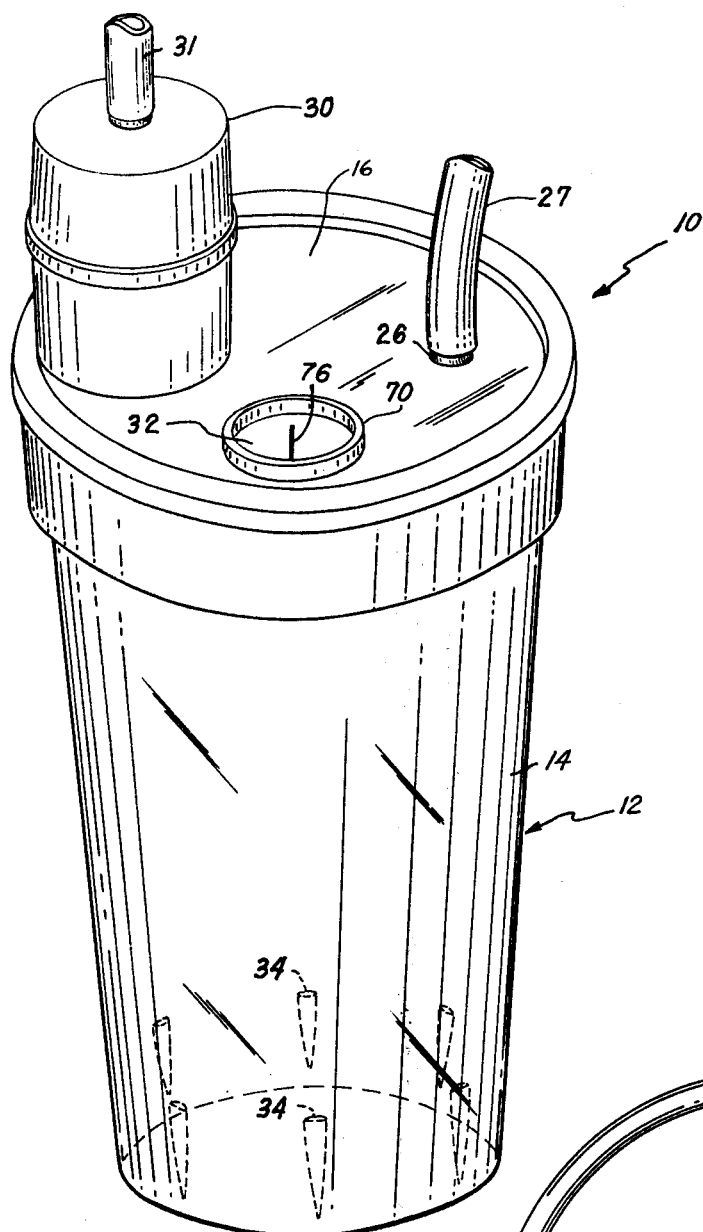
FIG. 1 is a perspective view of the assembled fluid collection apparatus with the vacuum line filter and connecting tubes in place.

Turning now to a more detailed consideration of the drawings, there is illustrated at 12 in FIG. 1 a body fluid container for use with an aspirator and having a generally cylindrical body portion having a sidewall 14, and a lid 16 adapted to engage the enlarged mouth 18 and its terminal bead 19 of the container and be lockably secured thereto. Formed as a part of the lid 16 are two generally tubular ports, inlet port or nipple 26 shown with a drainage tube 27 attached, and vacuum nipple 28, best seen in FIG. 3, adapted to be attached to a source of vacuum or to vacuum line filter 30 by a tube 31. The relief valve is shown generally at 32.

Additional details of the aspirator jar of the present invention are illustrated in FIG. 3 which is a cross-sectional view of the device of FIG. 1. As shown, the body portion 12 of the container includes a generally cylindrical wall 14, which preferably is tapered so that one container may be nested inside another for storage purposes. Thus, the wall 14 tapers inwardly from the mouth at 18 toward the bottom wall 33. A plurality of small projections or shoulders 34, are formed on the inner surface of the container wall 14, the shoulders being at a common height from the bottom of the container to define a stacking line. Thus the shoulders of one container are adapted to receive the bottom of a container nested within it to prevent the inner nested container from becoming wedged in the outer container, thus assuring easy removal. The wall 14 is relatively thin, preferably less than about 0.10 inch in thickness, and may be molded from a styrene-containing polymer or other suitable plastic material. The outwardly projecting mouth flange portion 18 of container 12 terminates at its top in a outwardly projecting bead 19.

An upwardly raised sealing ring 36 at the periphery of lid 16 has a peripheral pendant flange 37 formed with a cavity 38 adapted to receive and retain the peripheral edge and bead 19 of the container. The flange 37 at its lower end has an outwardly flared surface 40 forming a cam surface to facilitate entrance of the bead into the cavity. Sealing ring 36 has a second pendant sealing flange 42 spaced inwardly from flange 37, and flange 42 has an outer surface engaging the inner surface of the container in a substantially face to face engagement for sealing the lid to the container.

When the lid 16 is applied to the top of the container 12 so that the outwardly flared cam surface 40 engages the bead 19, downward pressure applied to the lid causes the cam surface of flange 37 to deflect outwardly relative to the bead and pass over the beat until the bead is securely retained within the cavity 38 and the sealing surfaces of flange 42 and the upper wall of the container are in face to face engagement.

The lid 16 is formed with intersecting ribs 44, best seen in FIG. 6, on the lower surface thereof. These ribs can form varying patterns in order to strengthen the lid and substantially prevent deformation thereof under vacuum. Extending downwardly from the ribs, as shown in FIG. 3, there are provided four retaining pins 46. The pins are equiangularly spaced and placed near the outer edge of the lid to provide means for mounting and securing a bag mounting ring 48, as shown in FIG. 5, which carries a bag-liner 50. A valve-support post 52 (FIG. 3) is provided to carry the floatable plastic or rubber pad 54, shown in FIGS. 3 and 5, which functions as an overflow valve to seal off the vacuum conduit by blocking the enlarged inlet chamber 56 in the pendant portion of nipple 28 when forced upward by its bouyancy in the fluid. The valve pad 54 can be made of any suitable non-porous plastic or rubber material with low specific gravity.

Figure 7:
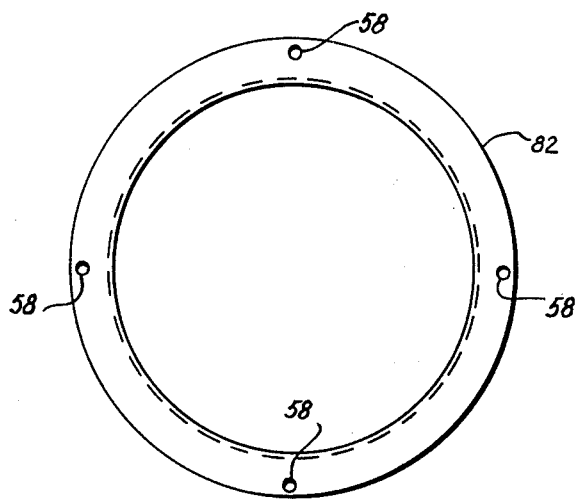
FIG. 7 is a plan view of the mounting flange for the bag liner.
Figure 8:
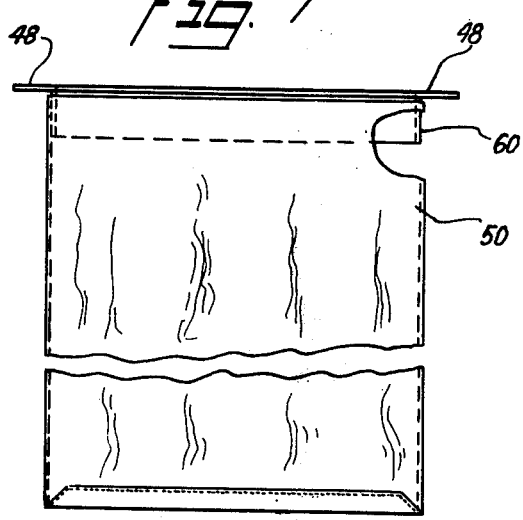
FIG. 8 is a side elevational fragmentary veiw of the flange with bag liner in place, a portion of the bag being cut away.

The pins 46 are placed to match a series of holes 58 (FIG. 7) in the upper flange of the bag mounting ring 48. In practice the bag itself, which is made of a flexible plastic material, can be fastened to the internally depending flange 60 of the mounting ring 48 and shown in FIG. 8. The bag can be secured to the depending flange by means of a suitable adhesive or by heat sealing it to the flange 60.

As shown in FIG. 5, the bag liner is placed in the apparatus by positioning the ring so that pins 46 pass through holes 58. The pins are then deformed by heat, or otherwise, to form a rivet-like head shown at 62 in FIGS. 5 and 6. The bag and its mounting ring are of course proportioned to enclose the pendant portion 64 of the fluid inlet nipple and its associated deflector chute 66 and the vacuum port chamber 56 with its associated overflow valve 54 so that the fluid flows into the bag and is collected therein.

Iat will be appreciated that the apparatus can be provided and used with or without the bag liner, depending on the needs and desires of the user.

Figure 9:
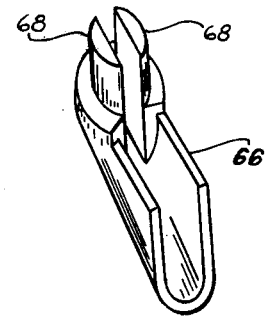
FIG. 9 is a perspective view of the deflector chute removed from the inlet port showing the means of attachment.

Referring again to FIGS. 3 and 5 it may be seen that the tubular inlet and outlet nipples 26 and 28 and their pendant portions are formed as an integral part of the lid structure, thereby eliminating the possibility of leaks in the system at the points where the inlet and outlet fittings pass into the container. The upper end of the inlet nipple 26 is elongated and slightly tapered to receive a tube, catheter or other conduit, leading, for example, from a patient from whom fluids are to be aspirated. Inlet opening in the pendant portion 64 of the inlet nipple is sufficiently large to securely receive the prongs 68 of deflector chute 66 as shown in FIGS. 6 and 9.

Again referring to FIG. 3 and 5 it will be seen that the outlet nipple 28 is adapted to receive suitable tubing or conduit means for connecting the nipple and thus the interior of container 12 to a suitable vacuum source (not shown) or to receive the vacuum line filter 30, to which the vacuum line tube 31 is in turn attached as shown in FIG. 1.

Figure 2:
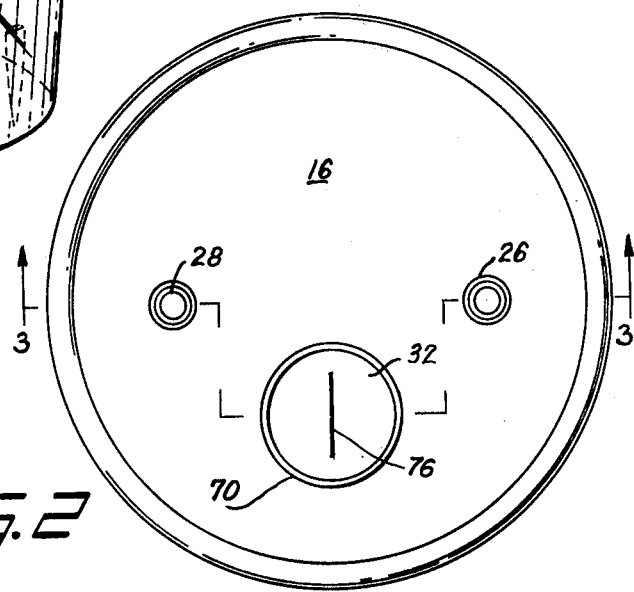
FIG. 2 is a plan view of the container lid of the present invention.

The lid is also provided with relief valve means such as the pressure relief valve shown generally at 32 in FIG. 1 to permit inward flow of air in the event the pressure inside the collection apparatus drops too low causing a danger of implosion. The preferred valve means comprises a circular cup having a side wall 70, shown in FIGS. 1 and 2, and a floor 72 which has a circular aperture 74 centrally located within the cup as shown in FIG. 6.

Figure 10:
FIG. 10 is a perspective view of the relief valve.

Located within the cup is the deformable nonporous plastic disk 32 shown in FIG. 10. The disk is provided with a generally centrally located slit 76 which coincides with the aperture 74. The length of the slit is preferably slightly longer than the diameter of the aperture. Under the influence of a predetermined critical pressure differential between the ambient atmospheric pressure and the negative pressure created by the vacuum system the slit will deform downwards into the aperture causing the edges to separate and allowing air to bleed into the collection apparatus until the stress in the disk is relieved at which point it will regain its original dimensions with the edges of the slit realigned and thus seal the aperture shutting off the inflow of air.

The vacuum line is protected from contamination by entrained moisture droplets to entrap such material without unduly restricting the volume of air flowing through the overall apparatus to the vacuum source. Since the operating efficiency of the aspirator device is in large measure dependent on the volume of air drawn through, it is important to maintain this function at the desired level. In general mechanical filters utilizing porous substances as a filter media must be carefully designed so as not to reduce the volume of air flow that level necessary to proper operation. A more suitable type of non-restricting filter or separator employs the effects of gravity or inertia to separate heavier-than-air matter as shown generally at 30 in FIGS. 1 and 3.

Figure 12:
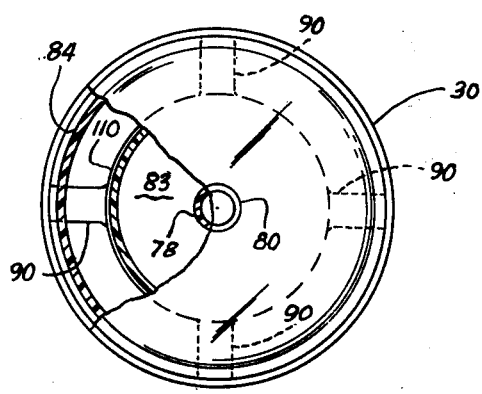
FIG. 12 is a top view of the vacuum line filter partly in section along line 12—12 of FIG. 3.

Referring to FIGS. 3 and 12, the separator comprises an inlet conduit 78 for placement over the vacuum nipple 28, an outlet nipple 80 adapted to be connected to tubing 31, as shown in FIG. 1, a lower wall portion 82 closed at its bottom 83, an upper wall portion 84 closed at the top except for the nipple portion 80, and a cup-shaped baffle shown generally at 86. The baffle comprises a depending skirt and a baffle surface 88. The baffle is held in place by supports 90 of which there may be two or more as needed. The baffle is positioned over the orifice of the inlet 78 so as to deflect the air flow downwardly into the collection chamber shown at 92 in FIG. 3. The collection chamber is defined by the lower wall portion 82 and the baffle 86 has a substantially larger volume than the inlet 78 so that as air passes through the inlet it expands and experiences a decrease in velocity. Impingement of the air on the baffle surface 88 causes some turbulence and a change in direction. The resulting decrease in flow rate together with turbulence and change of direction caused by deflection by baffle surface 88 causes entrained liquid and particulate matter which is heavier than air to drop into and remain in the collection chamber, the air then passes upwardly through apertures defined by baffle supports 90 and around the upper surface of the baffle to the outlet 80. The air flow is shown generally by indicator arrows in FIG. 3.

It will be appreciated that the above described separator or filter can be employed in any position relative to the container, i.e., horizontal or vertical. Best results however are obtained when the separator is so placed that the direction of air flow is vertical.

Figure 11:
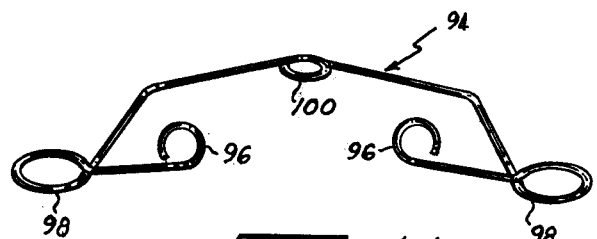
FIG. 11 is a perspective view of a conductive metal clip for connecting the tubing of the vacuum system to provide a complete electrical path to eliminate electrical discharges.

It will be understood that the tubing used in hospital operating areas is customarily provided with wires embedded in the tube walls and exposed at the tube ends as by bending back a projecting wire end. It is therefore proposed that a bent wire clip 94, as shown in FIG. 11, be furnished with each lid 16. The wire ends are circularly bent at 96 for engagement around the ends of tubes 27 and 31, as shown in FIG. 1. Coils or circular loops are formed at 98 and 100 to provide flexibility in the clip so that one circularly bent end 96 may be secured to the tube 31 whether it is secured to the nipple 28 of the lid or to the nipple 80 of filter 30. The clip 94 provides an electrical path in the operating area between tubes 27 and 31 to eliminate electrical discharges caused by static electricity.

As is customary in aspirator jars, the container 12 may have a graduated scale for showing the fluid contents in the container etched on the container sidewall. It is preferred, however, to furnish a paper strip, now shown, adhesively secured to the outer surface of sidewall 14 having such a scale printed thereon. Such a strip may also contain data such as the patient's name, date of use and such other written data as may be required.

We claim:

1. An aspirator jar for receiving and holding fluids comprising:
    a container having a closed bottom, a substantially cylindrical sidewall, and an open mouth portion defined by an annular, outwardly flared beaded rim formed at the top edge of said sidewall;
    a lid for said container adapted to engage the rim of said container and having means adapted to engage said rim to provide an airtight seal between the lid and the container;
    a pressure relief valve in an aperture in said lid communicating with the interior of said jar;
    said pressure relief valve comprising a slitted deformable disk placed over said aperture in said lid with said slit generally lying along the diameter of said aperture;
    a generally tubular inlet port and associated inlet chamber in said lid for admitting fluid to the interior of said container;
    a deflector chute attached to said inlet chamber for directing said fluid against said sidewall;
    a generally tubular outlet port and outlet chamber in said lid for use in withdrawing air from the interior of said container, whereby a negative pressure may be developed within the container; and
    an overflow valve assembly secured to said outlet chamber, said valve assembly including a float responsive to the level of fluid in said container for opening and closing said outlet chamber.

* * * * *